(12) United States Patent
Bridgeman et al.

(10) Patent No.: US 8,721,659 B2
(45) Date of Patent: May 13, 2014

(54) ADJUSTABLE WIRE LENGTH STYLET HANDLE

(75) Inventors: Elliot Bridgeman, Big Lake, MN (US);
Tom Walch, Centerville, MN (US);
Lawrence Kane, Roseville, MN (US)

(73) Assignee: Greatbatch Ltd., Clarence, NY (US)

( * ) Notice: Subject to any disclaimer, the term of this patent is extended or adjusted under 35 U.S.C. 154(b) by 313 days.

(21) Appl. No.: 13/222,018

(22) Filed: Aug. 31, 2011

(65) Prior Publication Data
US 2013/0053865 A1 Feb. 28, 2013

(51) Int. Cl.
*A61B 17/00* (2006.01)
*A61N 1/05* (2006.01)

(52) U.S. Cl.
USPC ............................. 606/129; 607/116; 607/117

(58) Field of Classification Search
None
See application file for complete search history.

(56) References Cited

U.S. PATENT DOCUMENTS

| | | | |
|---|---|---|---|
| 5,117,839 A * | 6/1992 | Dance | 600/585 |
| 5,238,004 A | 8/1993 | Sahatjian et al. | |
| 5,254,088 A * | 10/1993 | Lundquist et al. | 604/95.04 |
| 5,957,966 A | 9/1999 | Schroeppel et al. | |
| 6,168,571 B1 | 1/2001 | Solar et al. | |
| 6,214,016 B1 | 4/2001 | Williams et al. | |
| 6,270,496 B1 | 8/2001 | Bowe | |
| 2009/0240258 A1* | 9/2009 | Kuzma et al. | 606/129 |
| 2009/0281524 A1* | 11/2009 | Scheibe et al. | 604/528 |

* cited by examiner

*Primary Examiner* — Melanie Tyson
*Assistant Examiner* — Todd J Scherbel
(74) *Attorney, Agent, or Firm* — Michael P. Horvath

(57) ABSTRACT

A stylet-lead assembly includes a therapy delivery element and a stylet. The therapy delivery element includes a proximal end, a distal end, and a lumen having a lumen length extending from the proximal end to almost the distal end. The stylet includes a stylet handle including a locking insert having a first channel adapted to receive a proximal end of a stylet wire. A portion of the stylet wire extending beyond a proximal end of the locking insert includes at least one bend. The stylet handle has an opening at a distal end adapted to compressively engage the proximal end of the stylet wire to the locking insert, such that an exposed portion of the stylet wire measured from a distal end of the stylet wire to a distal end of the locking insert generally comprises the lumen length.

18 Claims, 8 Drawing Sheets

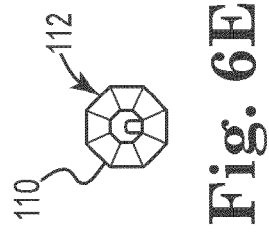
Fig. 6E
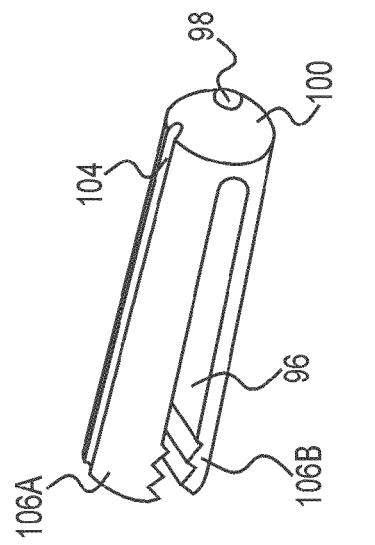
Fig. 6D
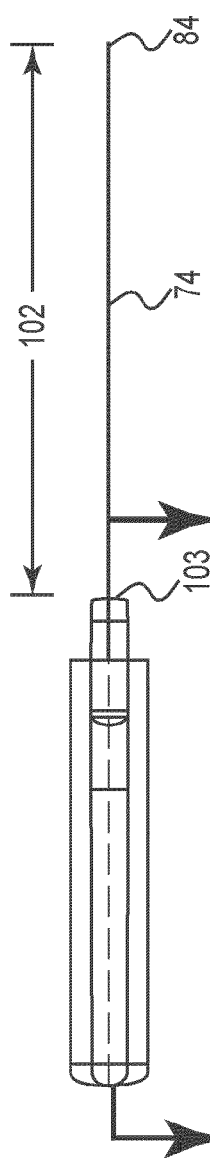
Fig. 6A
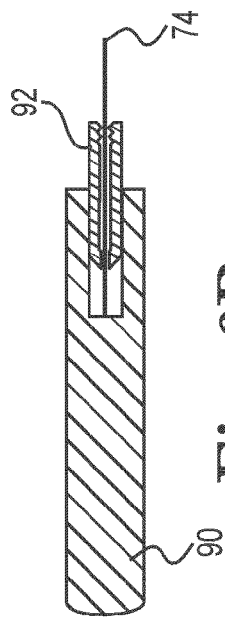
Fig. 6B
Fig. 6C

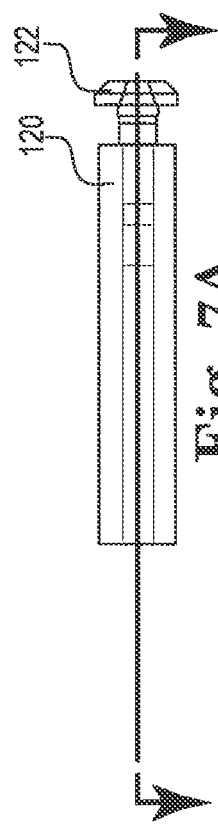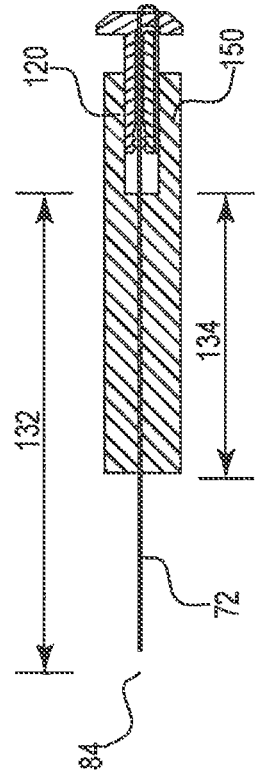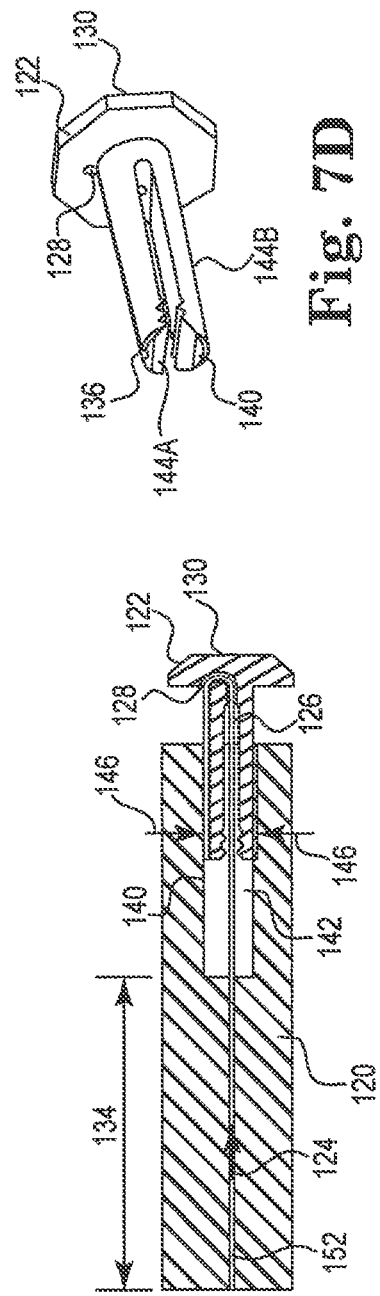

ADJUSTABLE WIRE LENGTH STYLET HANDLE

FIELD

The present disclosure relates to a stylet handle that permits the stylet wire length to be easily adjusted during manufacturing or by the surgeon.

BACKGROUND

Spinal cord stimulation requires a lead/stylet assembly that has a very high resistance to kinks and high buckling strength since the lead/stylet assembly is pushed through muscle, fascia and other tissue. The lead should preferably have a small diameter profile to facilitate ease of insertion into tissue. Because the lead has a small diameter, the stylet wire, by necessity, must also have a small diameter profile in order to fit inside the lead lumen. At the same time, the lead/stylet should preferably offer mechanical characteristics which enable multiple insertions into tissue, without breaking or permanently bending. Currently several types of lead-stylet assemblies exist for this purpose. An example of a stylet that engages the proximal end of the lead connector region in specified locations is the Pisces Quad Lead Model 3487A stylet available from Medtronic, Inc., Minneapolis, Minn., USA.

The location of the distal end of the stylet can potentially reside in different locations in the electrode region of the lead due to manufacturing tolerances in both the lead and the stylet. Manufacturing variability in the leads often requires the length of the stylet wires to be custom cut. Since the distal end of the stylet wire is typically prepared with a rounded tip that will not damage the lead during insertion, the stylet wire needs to be cut at the proximal end.

Stylet handles are typically overmolded onto the stylet wire or two half pieces are snapped over the stylet wire. These manufacturing techniques make it difficult to adjust the length of the stylet wire for different lengths and tolerances for these therapy delivery elements.

BRIEF SUMMARY

The present disclosure relates to a stylet handle that permits the stylet wire length to be easily adjusted during manufacturing or by the surgeon.

One embodiment is directed to stylet-lead assembly including a therapy delivery element and a stylet. The therapy delivery element includes a proximal end with a plurality of electrical contacts adapted to electrically couple with an implantable pulse generator, a distal end with a plurality of electrodes electrically coupled to the electrical contacts, and a lumen having a lumen length extending from the proximal end to almost the distal end. The stylet handle includes a locking insert having a first channel adapted to receive the proximal end of the stylet wire. The portion of the stylet wire extending beyond the proximal end of the locking insert includes at least one bend. A stylet handle has an opening at a distal end adapted to compressively engage the proximal end of the stylet wire to the locking insert, such that an exposed portion of the stylet wire measured from the distal end of the stylet wire to a distal end of the locking insert generally comprises the lumen length.

In one embodiment the locking insert includes a second channel adapted to receive a portion of the stylet wire extending beyond the proximal end of the locking insert. The first channel is preferably generally parallel to the second channel.

In another embodiment, the portion of the stylet wire extending beyond a proximal end of the locking insert includes a bend of about 180 degrees located between the first channel and the second channel. The second channel is typically formed in an outer surface of the locking insert.

In another embodiment, the first channel includes a pair of arms adapted to flex inward to compressively engage the proximate end of the stylet wire. The pair of arms preferably includes a cross-sectional area greater than a cross-sectional area of the opening in the stylet handle.

Another embodiment is directed to an alternate stylet-lead assembly with a stylet handle having a handle lumen extending from a distal end to an opening at a proximal end. The proximal end of the stylet wire extends through the handle lumen and has at least one bend located in the opening. The opening is adapted to compressively engage the stylet wire to the locking insert, such that an exposed portion of the stylet wire measured from the distal end of the stylet wire to the distal end of the stylet handle generally comprises the lumen length.

The present disclosure is also directed to a neurostimulation system including an implantable pulse generator. The therapy delivery element comprising a proximal end with a plurality of electrical contacts adapted to electrically couple with the implantable pulse generator. A stylet wire with a stylet handle in accordance with the present disclosure is located in a lumen in the therapy delivery element.

The present disclosure is also directed to a method of making a stylet-lead assembly. The proximal end of a stylet wire is inserted into a first channel in a locking insert such that an exposed portion of the stylet wire measured from a distal end of the stylet wire to a distal end of the locking insert generally has a length corresponding to a length of a lumen in the therapy delivery element. The portion of the stylet wire extending beyond a proximal end of the locking insert is bent. The portion of the stylet wire extending beyond a proximal end of the locking insert is located in a second channel on the locking insert. The proximal end of the locking insert is inserted in an opening in a distal end of a stylet handle. The stylet wire and the locking insert are compressively engaged by the stylet handle. The distal end of the stylet wire is inserted in a lumen accessible at a proximal end of a therapy delivery element.

The present disclosure is also directed to a method of implanting a neurostimulation system within a living body. The method includes grasping the stylet handle to steer the electrodes at a distal end of a therapy delivery element to a target location within the living body. The stylet is removed from the therapy delivery element. The implantable pulse generator is implanted within the living body. The proximal end of the therapy delivery element is electrically coupled with the implantable pulse generator.

BRIEF DESCRIPTION OF THE SEVERAL VIEWS OF THE DRAWING

FIGS. 6A-6E are various views of a stylet in accordance with an embodiment of the present disclosure.

FIGS. 7A-7D are various views of a stylet in accordance with an embodiment of the present disclosure.

DETAILED DESCRIPTION OF SOME EMBODIMENTS

The description that follows relates to a spinal cord stimulation (SCS) system. However, it is to be understood that the while the present disclosure lends itself well to applications in SCS, the disclosure in its broadest aspects may not be so limited. Rather, the disclosure may be used with any type of implantable therapy delivery system with one or more therapy delivery elements. For example, the present disclosure may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

In another embodiment, one or more of the therapy delivery elements may be a fluid delivery conduit, such as a catheter, including an inner lumen that is placed to deliver a fluid, such as pharmaceutical agents, insulin, pain relieving agents, gene therapy agents, or the like from a fluid delivery device (e.g., a fluid reservoir and/or pump) to a respective target tissue site in a patient.

In yet another embodiment, one or more of the therapy delivery elements may be an electrical lead including one or more sensing electrodes to sense physiological parameters (e.g., blood pressure, temperature, cardiac activity, etc.) at a target tissue site within a patient. In the various embodiments contemplated by this disclosure, therapy may include stimulation therapy, sensing or monitoring of one or more physiological parameters, fluid delivery, and the like. "Therapy delivery element" includes pacing or defibrillation leads, stimulation leads, sensing leads, fluid delivery conduit, and any combination thereof "Target tissue site" refers generally to the target site for implantation of a therapy delivery element, regardless of the type of therapy.

Figure 1:
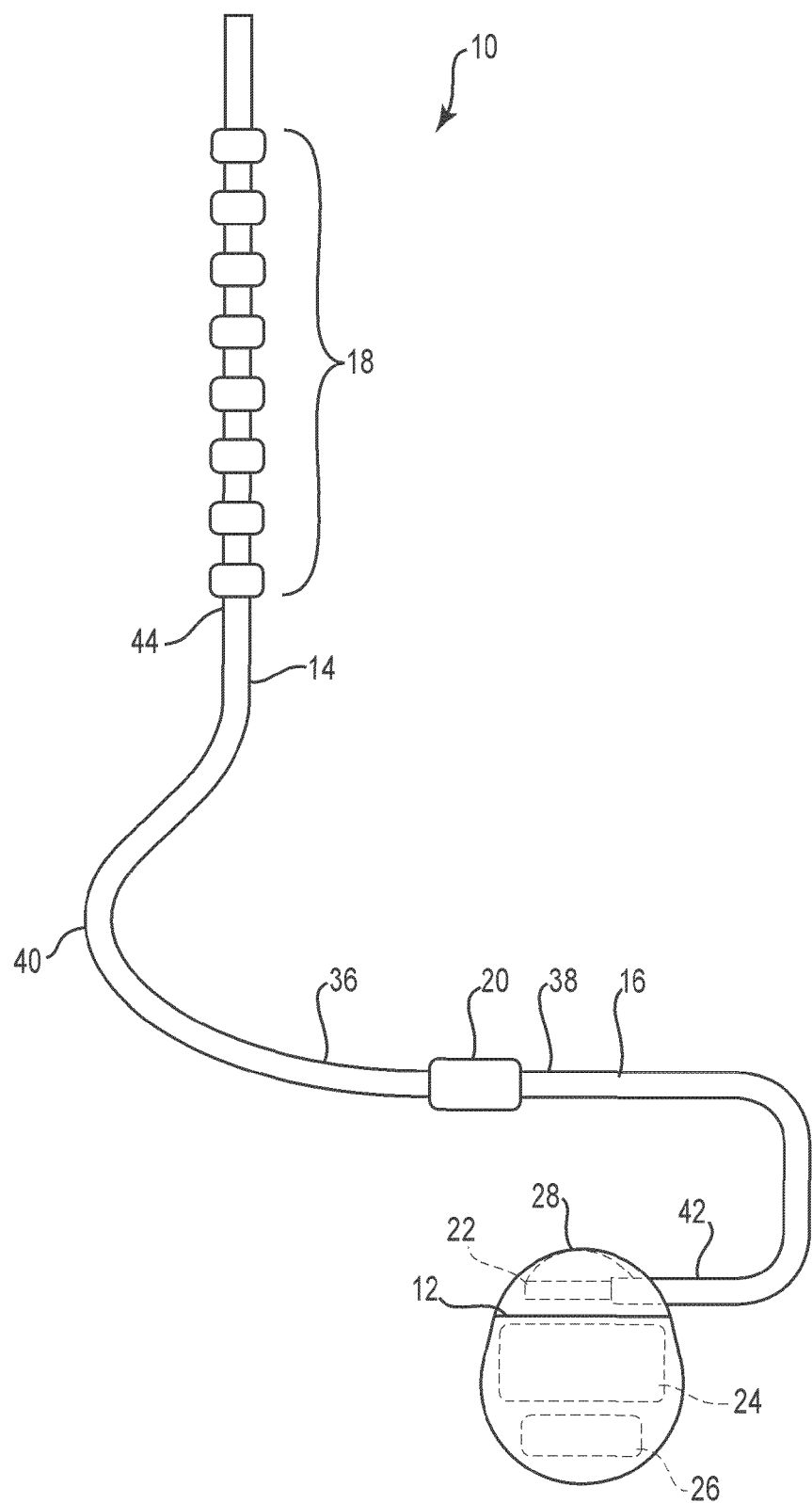
FIG. 1 is a schematic illustration of a therapy delivery system.

FIG. 1 illustrates a generalized therapy delivery system 10 that may be used in spinal cord stimulation (SCS), as well as other stimulation applications. The therapy delivery system 10 generally includes an implantable pulse generator 12 ("IPG"), an implantable therapy delivery element 14, which carries an array of electrodes 18 (shown exaggerated for purposes of illustration), and an optional implantable extension lead 16. Although only one therapy delivery element 14 is shown, typically two or more therapy delivery elements 14 are used with the therapy delivery system 10.

The therapy delivery element 14 includes elongated body 40 having a proximal end 36 and a distal end 44. The elongated body 40 typically has a diameter of between about 0.03 inches to 0.07 inches and a length within the range of 30 cm to 90 cm for spinal cord stimulation applications. The elongated body 40 may be composed of a suitable electrically insulative material, such as, a polymer (e.g., polyurethane or silicone), and may be extruded as a uni-body construction.

In the illustrated embodiment, proximal end 36 of the therapy delivery element 14 is electrically coupled to distal end 38 of the extension lead 16 via a connector 20, typically associated with the extension lead 16. Proximal end 42 of the extension lead 16 is electrically coupled to the implantable pulse generator 12 via connector 22 associated with housing 28. Alternatively, the proximal end 36 of the therapy delivery element 14 can be electrically coupled directly to the connector 22.

In the illustrated embodiment, the implantable pulse generator 12 includes electronic subassembly 24 (shown schematically), which includes control and pulse generation circuitry (not shown) for delivering electrical stimulation energy to the electrodes 18 of the therapy delivery element 14 in a controlled manner, and a power supply, such as battery 26.

The implantable pulse generator 12 provides a programmable stimulation signal (e.g., in the form of electrical pulses or substantially continuous-time signals) that is delivered to target stimulation sites by electrodes 18. In applications with more than one therapy delivery element 14, the implantable pulse generator 12 may provide the same or a different signal to the electrodes 18.

Alternatively, the implantable pulse generator 12 can take the form of an implantable receiver-stimulator in which the power source for powering the implanted receiver, as well as control circuitry to command the receiver-stimulator, are contained in an external controller inductively coupled to the receiver-stimulator via an electromagnetic link. In another embodiment, the implantable pulse generator 12 can take the form of an external trial stimulator (ETS), which has similar pulse generation circuitry as an IPG, but differs in that it is a non-implantable device that is used on a trial basis after the therapy delivery element 14 has been implanted and prior to implantation of the IPG, to test the responsiveness of the stimulation that is to be provided.

The housing 28 is composed of a biocompatible material, such as for example titanium, and forms a hermetically sealed compartment containing the electronic subassembly 24 and battery 26 and protecting the electronic subassembly 24 and battery 26 from the body tissue and fluids. The connector 22 is disposed in a portion of the housing 28 that is, at least initially, not sealed. The connector 22 carries a plurality of contacts that electrically couple with respective terminals at proximal ends of the therapy delivery element 14 or extension lead 16. Electrical conductors extend from the connector 22 and connect to the electronic subassembly 24.

Figure 2:
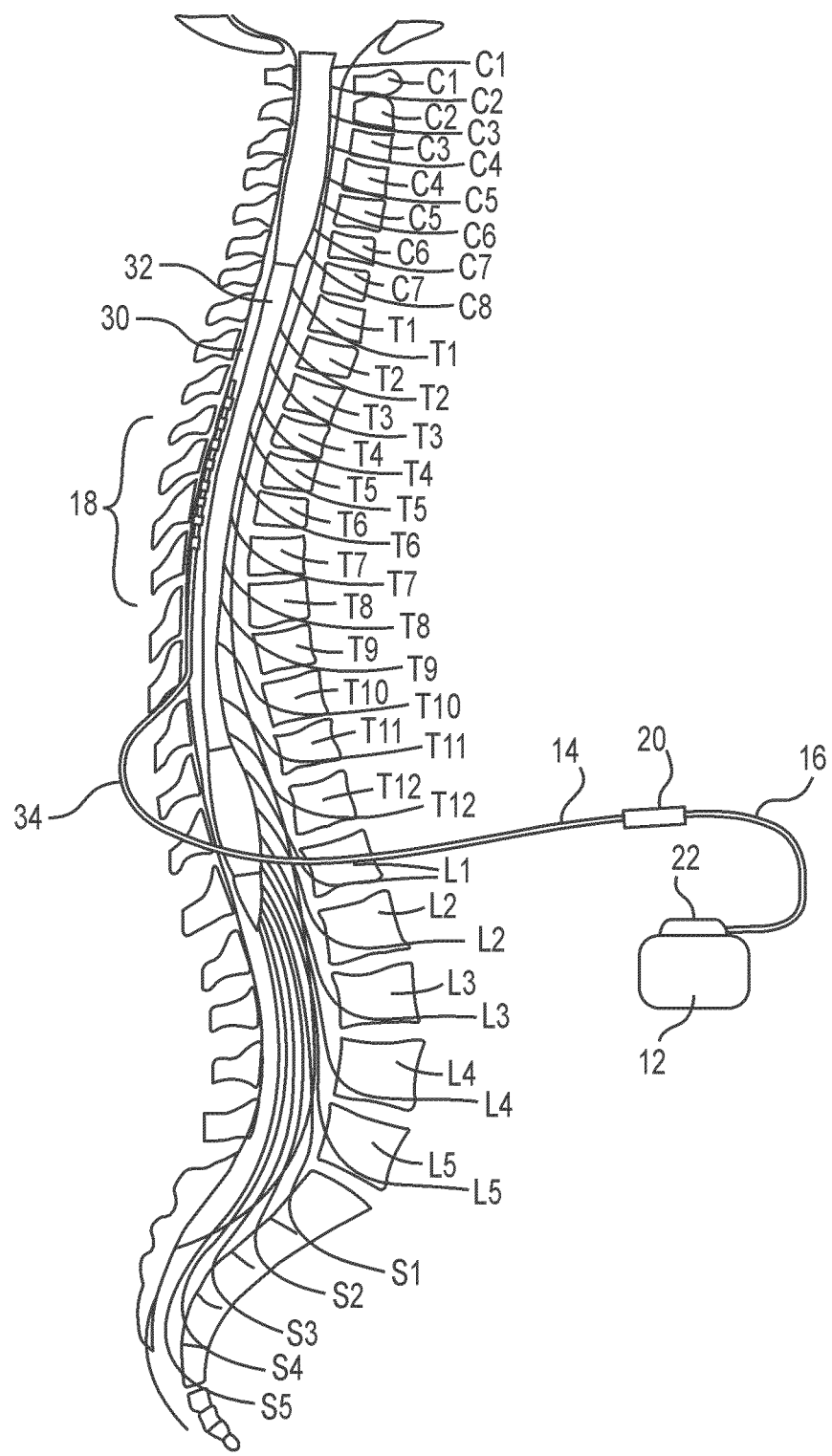
FIG. 2 is a schematic illustration of an environment for a therapy delivery system in accordance with an embodiment of the present disclosure.

FIG. 2 illustrates the therapy delivery element 14 implanted in the epidural space 30 of a patient in close proximity to the dura, the outer layer that surrounds the spinal cord 32, to deliver the intended therapeutic effects of spinal cord electrical stimulation. The target stimulation sites may be anywhere along the spinal cord 32, such as for example proximate the sacral nerves.

Figure 3:
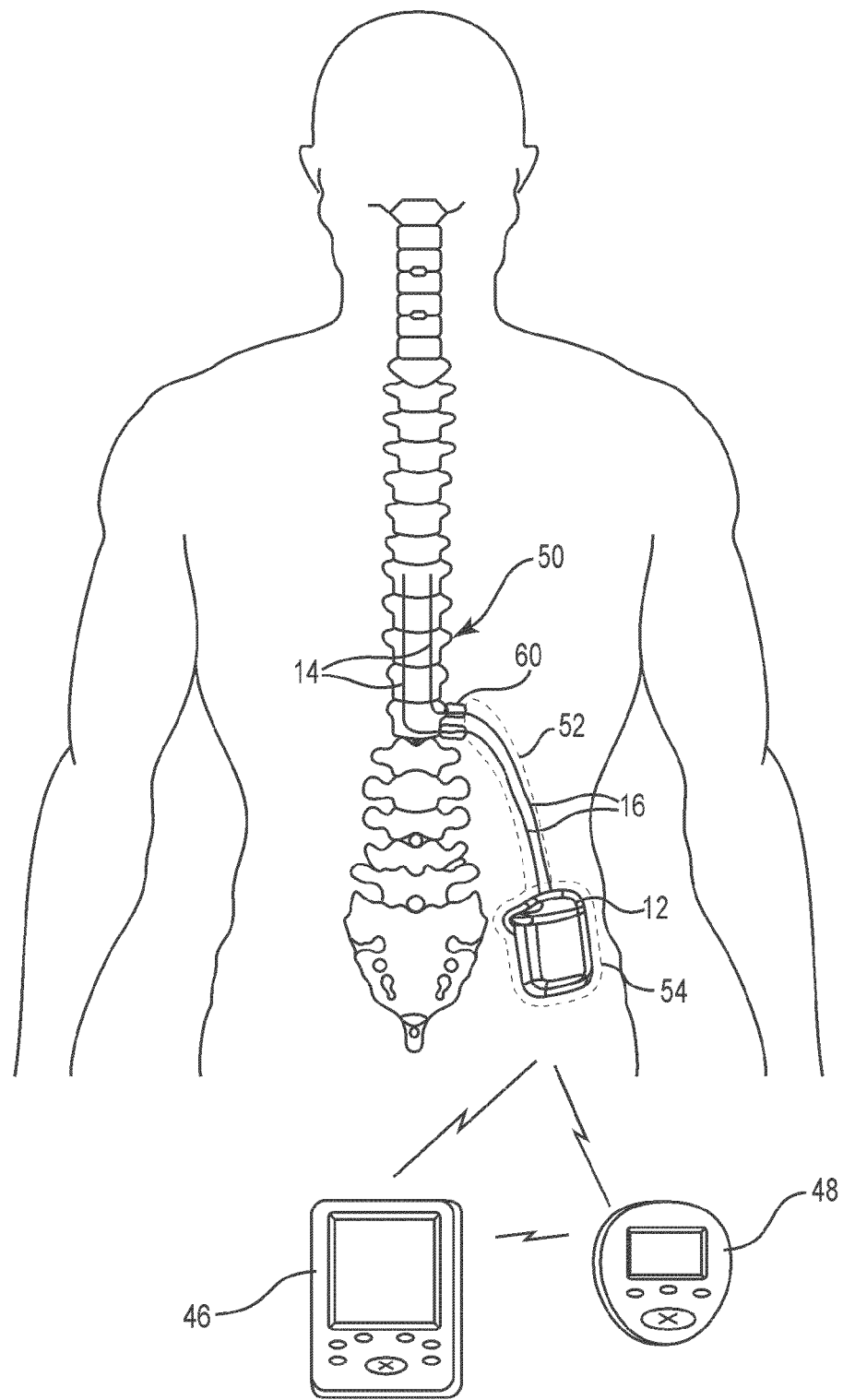
FIG. 3 is an alternate illustration of the environment for an implantable pulse generator with a therapy delivery element in accordance with an embodiment of the present disclosure.

Because of the lack of space near the lead exit point 34 where the therapy delivery element 14 exits the spinal column, the implantable pulse generator 12 is generally implanted in a surgically-made pocket either in the abdomen or above the buttocks, such as illustrated in FIG. 3. The implantable pulse generator 12 may, of course, also be implanted in other locations of the patient's body. Use of the extension lead 16 facilitates locating the implantable pulse generator 12 away from the lead exit point 34. In some embodiments, the extension lead 16 serves as a lead adapter if the proximal end 36 of the therapy delivery element 14 is not compatible with the connector 22 of the implantable pulse generator 12, since different manufacturers use different connectors at the ends of their stimulation leads and are not always compatible with the connector 22.

As illustrated in FIG. 3, the therapy delivery system 10 also may include a clinician programmer 46 and a patient programmer 48. Clinician programmer 46 may be a handheld computing device that permits a clinician to program neurostimulation therapy for patient using input keys and a display. For example, using clinician programmer 46, the clinician may specify neurostimulation parameters for use in delivery of neurostimulation therapy. Clinician programmer 46 supports telemetry (e.g., radio frequency telemetry) with the implantable pulse generator 12 to download neurostimulation parameters and, optionally, upload operational or physiological data stored by implantable pulse generator 12. In this manner, the clinician may periodically interrogate the implantable pulse generator 12 to evaluate efficacy and, if necessary, modify the stimulation parameters.

Similar to clinician programmer 46, patient programmer 48 may be a handheld computing device. Patient programmer 48 may also include a display and input keys to allow patient to interact with patient programmer 48 and the implantable pulse generator 12. The patient programmer 48 provides patient with an interface for control of neurostimulation therapy provided by the implantable pulse generator 12. For example, patient may use patient programmer 48 to start, stop or adjust neurostimulation therapy. In particular, patient programmer 48 may permit patient to adjust stimulation parameters such as duration, amplitude, pulse width and pulse rate, within an adjustment range specified by the clinician via clinician programmer 46, or select from a library of stored stimulation therapy programs.

The implantable pulse generator 12, clinician programmer 46, and patient programmer 48 may communicate via cables or a wireless communication. Clinician programmer 46 and patient programmer 48 may, for example, communicate via wireless communication with the implantable pulse generator 12 using RF telemetry techniques known in the art. Clinician programmer 46 and patient programmer 48 also may communicate with each other using any of a variety of local wireless communication techniques, such as RF communication according to the 802.11 or Bluetooth specification sets, infrared communication, e.g., according to the IrDA standard, or other standard or proprietary telemetry protocols.

FIG. 3 also illustrates a general environment that may benefit from use of a tunneling tool in accordance with an embodiment of the present disclosure. Since the implantable pulse generator 12 is located remotely from target location 50 for therapy, the therapy delivery element 14 and/or the extension lead 16 is typically routed through a pathway 52 subcutaneously formed along the torso of the patient to a subcutaneous pocket 54 where the implantable pulse generator 12 is located. As used hereinafter, "lead" and "lead extension" are used interchangeably, unless content clearly dictates otherwise.

The therapy delivery elements 14 are typically fixed in place near the location selected by the clinician using the present suture anchors 60. The suture anchors 60 can be positioned on the therapy delivery element 14 in a wide variety of locations and orientations to accommodate individual anatomical differences and the preferences of the clinician. The suture anchors 60 may then be affixed to tissue using fasteners, such as for example, one or more sutures, staples, screws, or other fixation devices. The tissue to which the suture anchors 60 are affixed may include subcutaneous fascia layer, bone, or some other type of tissue. Securing the suture anchors 60 to tissue in this manner prevents or reduces the chance that the therapy delivery element 14 will become dislodged or will migrate in an undesired manner.

Figure 4A:
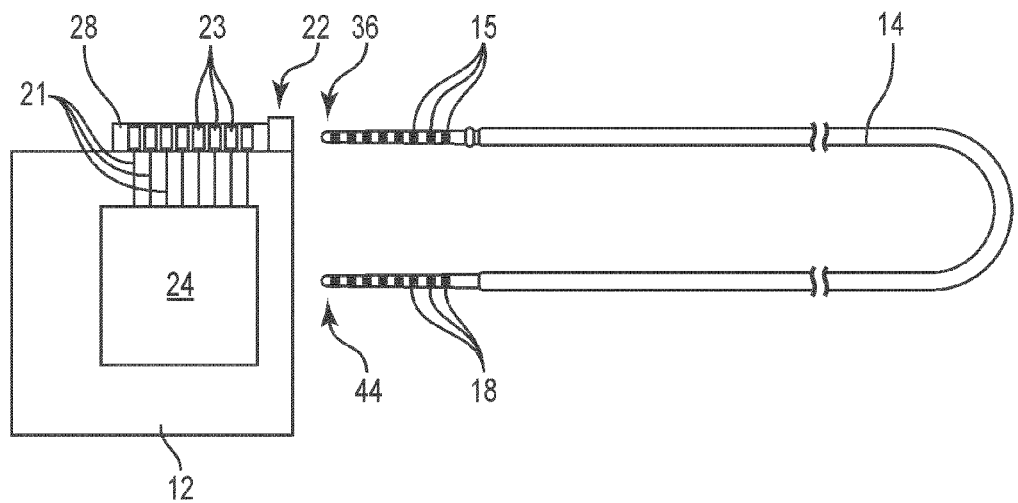
FIG. 4A is a schematic illustration of an implantable pulse generator and a therapy delivery element in accordance with an embodiment of the present disclosure.

FIG. 4A illustrates the therapy delivery element 14 including one or more electrical contacts 15 at the proximal end 36, and one or more electrodes 18 at the distal end 44. The contacts 15 and electrodes 18 are electrically coupled via insulated wires running through the therapy delivery element 14. Proximal end 36 of the therapy delivery element 14 is electrically and mechanically coupled to implantable pulse generator 12 by the connector assembly 22.

The connector assembly 22 includes a plurality of discrete contacts 23 located in the housing 28 that electrically couple contact rings 15 on the proximal end of the therapy delivery element 14. The discrete contacts 23 are electrically coupled to circuitry 24 in the implantable pulse generator 12 by conductive members 21. Each contact ring 15 is electrically coupled to one or more of the electrodes 18 located at the distal end 44 of the therapy delivery element 14. Consequently, the implantable pulse generator 12 can independently deliver electrical impulses to each of the electrodes 18.

Figure 4B:
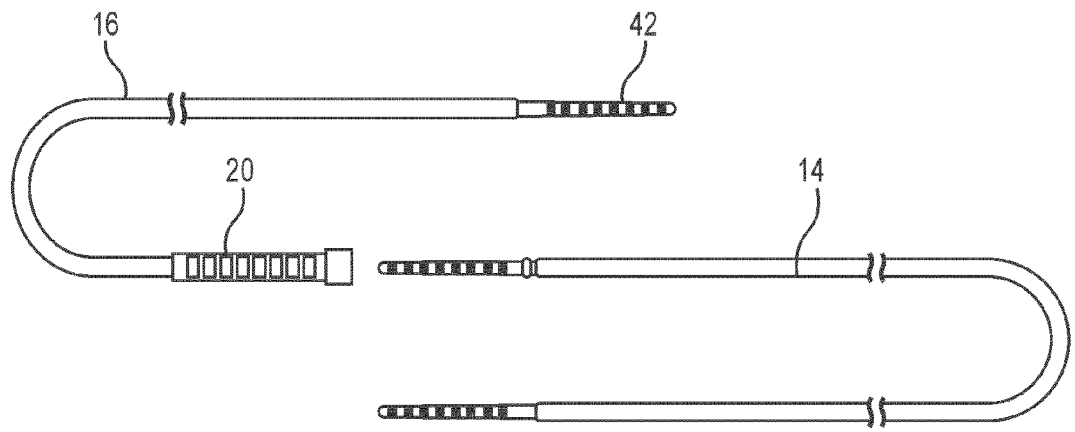
FIG. 4B is a schematic illustration of a lead extension and a therapy delivery element in accordance with an embodiment of the present disclosure.

Alternatively, the therapy delivery element 14 can be coupled to the implantable pulse generator 12 through one or more lead extensions 16, as illustrated in FIG. 4B. The connector 20 at the distal end 38 of the lead extension 16 preferably includes a plurality of the contacts 23 configured in a manner similar to the connector assembly 22 (See FIG. 4A.

Figure 5A:
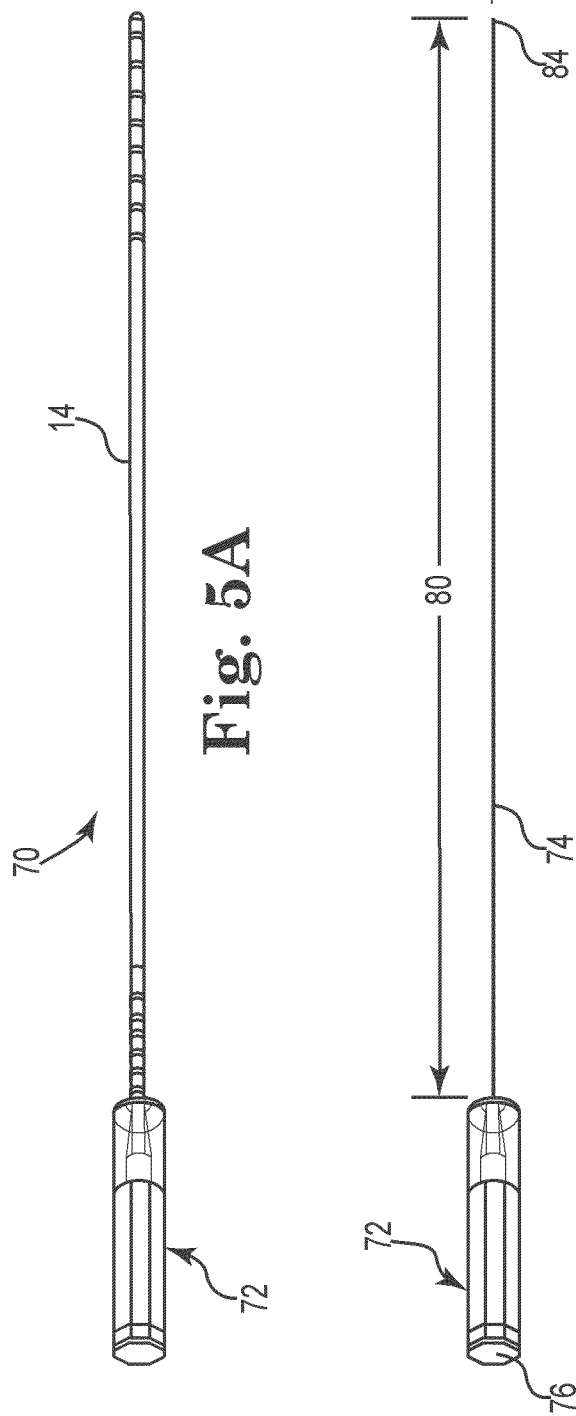
FIG. 5A is a schematic illustration of a stylet-lead assembly in accordance with an embodiment of the present disclosure.
Figure 5B:
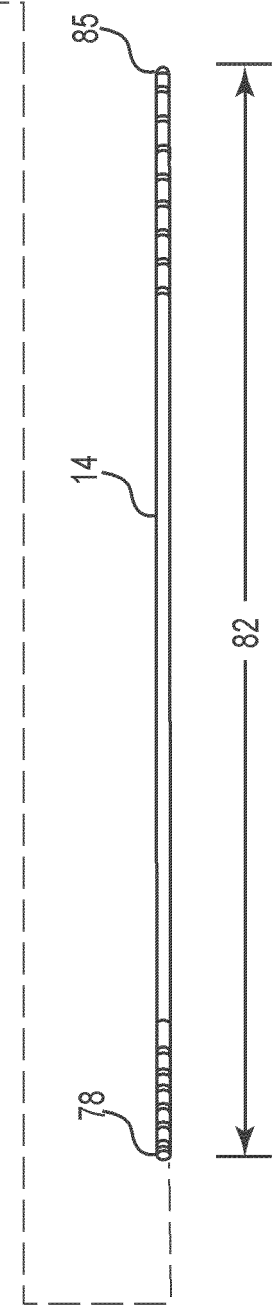
FIG. 5B is an exploded view of the stylet-lead assembly of FIG. 5A.

FIGS. 5A and 5B illustrate a stylet/lead assembly 70 including the therapy delivery element 14 and a stylet 72 in accordance with an embodiment of the present disclosure. The term stylet refers to a tool inserted into the lumen of a therapy delivery element, such as a neurostimulation lead, to stiffen the lead body and to facilitate its insertion into a target tissue.

In the illustrated embodiment, stylet 72 includes stylet wire 74 attached to handle 76. The stylet wire 74 has a diameter smaller than lumen 78 in the therapy delivery element 14 and length 80 less than length 82 of the lumen 78. The distal end 85 of the therapy delivery element is typically sealed, so the length 82 of the lumen 78 is less than the length of the therapy delivery element 14. In use, distal end 84 of the stylet wire 74 is inserted in lumen 78 of the therapy delivery element 14 to create the stylet/lead assembly 70.

Conventional stylet wires for the SCS application are typically made of stainless steel or tungsten. Tungsten is a malleable, linear elastic material. A stylet wire made from tungsten is flexible and does not easily break but, unfortunately, has poor kink resistance. "Kink resistance" refers to the ability of the stylet wire to be bent into a relatively tight bend radius without incurring permanent deformation.

Once a stylet wire 74 kinks, the stylet/lead assembly 70 may have to be withdrawn from the tissue because the permanent bend in the stylet wire 74 makes it difficult to steer the lead/stylet assembly 70 within the tissue. The ability to steer the therapy delivery element 14 is critical for achieving optimal stimulation in spinal cord stimulation where a positional difference of a few millimeters may mean the difference between poor or effective stimulation. If the stylet wire 74 kinks during use, both the stylet 72 and therapy delivery element 14 may need to be scrapped because the bent stylet wire 74 cannot be easily extracted from the lumen 78 without causing further damage to the therapy delivery element 14 or dislodging the therapy delivery element 14 from the tissue site.

Super-elastic materials provide excellent kink resistance but have poor resistance to buckling forces and torque. Consequently, a stylet wire 74 made from these materials alone is not be suitable for use for SCS therapy delivery elements. Stylet wires manufactured from combinations of linear and super-elastic materials have been evaluated, as disclosed in U.S. Pat. Nos. 6,214,016; 6,168,571; 5,238,004; 6,270,496 and 5,957,966, which are hereby incorporated by reference.

During manufacturing of the stylet 72, the length 80 of the stylet wire 74 needs to be matched with the length 82 of the lumen 78. If the length 80 of the stylet wire 74 is greater than the length 82 of the lumen 78, the therapy delivery element 14 is likely to be damaged during insertion. Alternatively, if the length 80 of the stylet wire 74 is less than the length 82 of the lumen 78, the therapy delivery element 14 will be difficult to steer into the epidural space 30.

FIGS. 6A-6E illustrate a stylet handle 90 with a locking insert 92 that captures the stylet wire 74 in accordance with an embodiment of the present disclosure. The stylet wire 74 is fed in through channel 96 and out opening 98 at proximal end 100 of the locking insert 92 until the exposed length 102 of the stylet wire 74 corresponds to the length 82 of the lumen 78. The exposed length 102 is measured from distal end 84 of the stylet wire 74 to distal end 103 of the locking insert 92.

Excess stylet wire 74A protruding beyond opening 98 is bent about 180 degrees and located in channel 104 on locking insert 92. In an alternate embodiment, the channel 104 can be formed in the opening 105 in the handle 90. As best illustrated in FIG. 6E, the stylet handle 90 has an octagonal cross-section 110 to facilitate gripping of the stylet 112 by the surgeon.

The proximal end 100 of the locking insert 92 is then inserted in opening 105 of the stylet handle 90. The opening 105 is sized to compress arms 106A, 106B on the locking insert 92 in direction 108 to lock the stylet wire 74 to the handle 90. The present locking insert 92 results in a more controllable manufacturing process than other techniques.

FIGS. 7A-7D illustrate an alternate stylet handle 120 with a locking insert 122 that captures the stylet wire 74 in accordance with an embodiment of the present disclosure. The stylet wire 74 is fed in direction 124 through channel 126 and out opening 128 at proximal end 130 of the locking insert 122 until the exposed length 132 of the stylet wire 74 corresponds to the length 82 of the lumen 78 plus length 134 of the handle lumen 152 in the handle 120. Excess stylet wire 74A protruding beyond opening 128 is bent about 180 degrees and located in channel 136 on locking insert 122.

Distal end 140 of the locking insert 122 is then inserted in opening 142 of the stylet handle 120. The opening 140 is sized to compress arms 144A, 144B on the locking insert 92 in direction 146 to lock the stylet wire 74 to the handle 120. A spacer with length 134 is optionally used to facilitate manufacturing the stylet 150.

Figure 8:
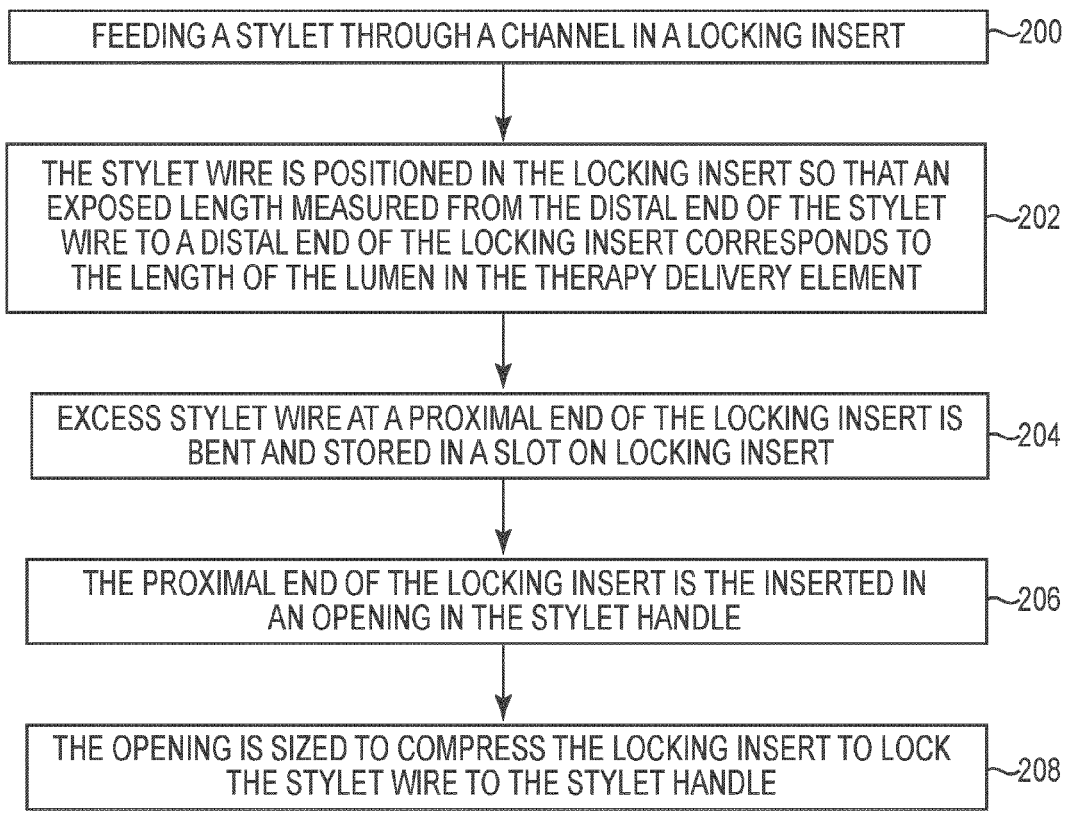
FIG. 8 is a flow chart of one method of making a stylet in accordance with an embodiment of the present disclosure.

FIG. 8 is a flow diagram of a method of manufacturing a stylet handle in accordance with an embodiment of the present disclosure. The method includes the steps of feeding a stylet wire through a channel in a locking insert (200). The stylet wire is positioned in the locking insert so that an exposed length measured from the distal end of the stylet wire to a distal end of the locking insert corresponds to the length of the lumen in the therapy delivery element (202). Excess stylet wire at a proximal end of the locking insert is bent and stored in a channel on locking insert (204). The proximal end of the locking insert is then inserted in an opening in the stylet handle (206). The opening is sized to compress the locking insert to lock the stylet wire to the stylet handle (208).

Where a range of values is provided, it is understood that each intervening value, to the tenth of the unit of the lower limit unless the context clearly dictates otherwise, between the upper and lower limit of that range and any other stated or intervening value in that stated range is encompassed within this disclosure. The upper and lower limits of these smaller ranges which may independently be included in the smaller ranges is also encompassed within the disclosure, subject to any specifically excluded limit in the stated range. Where the stated range includes one or both of the limits, ranges excluding either both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the various methods and materials are now described. All patents and publications mentioned herein, including those cited in the Background of the application, are hereby incorporated by reference to disclose and described the methods and/or materials in connection with which the publications are cited.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

Other embodiments are possible. Although the description above contains much specificity, these should not be construed as limiting the scope of the disclosure, but as merely providing illustrations of some of the presently preferred embodiments. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form varying modes disclosed. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

What is claimed is:
1. A stylet-lead assembly comprising:
  a therapy delivery element comprising a proximal end with a plurality of electrical contacts adapted to electrically couple with an implantable pulse generator, a distal end with a plurality of electrodes electrically coupled to the electrical contacts, and a lumen having a lumen length extending from the proximal end to almost the distal end;

a stylet wire having a distal end and a proximal portion including a proximal, terminal end;

a locking insert having a first channel adapted to receive the proximal portion of the stylet wire, wherein an excess portion of the proximal portion of the stylet wire extending beyond a proximal end of the locking insert includes at least one bend; and a stylet handle having an opening at a first end adapted to compressively engage the proximal portion of the stylet wire to the locking insert to lock the stylet wire with respect to the stylet handle, such that an exposed length of an exposed portion of the stylet wire extending distally from the stylet handle is generally equal to the lumen length, wherein:
the proximal, terminal end of the stylet wire is disposed within the stylet handle; and
with the proximal portion of the stylet wire compressively engaged with the locking insert, the exposed length of the stylet wire is fixed.

2. The stylet-lead assembly of claim 1, comprising a second channel in the locking insert adapted to receive the excess portion of the stylet wire extending beyond the proximal end of the locking insert.

3. The stylet-lead assembly of claim 2, wherein the first channel is generally parallel to the second channel.

4. The stylet-lead assembly of claim 2, wherein the at least one bend of the excess portion of the stylet wire includes a bend of about 180 degrees between the first channel and the second channel.

5. The stylet-lead assembly of claim 2, wherein the second channel is formed in an outer surface of the locking insert.

6. The stylet-lead assembly of claim 1, wherein the first channel is disposed between a pair of arms adapted to flex inwardly to compressively engage the proximal portion of the stylet wire.

7. The stylet-lead assembly of claim 6, wherein the pair of arms includes a cross-sectional area greater than a cross-sectional area of the opening in the stylet handle.

8. The stylet-lead assembly of claim 1, wherein the opening is at a proximal end of the stylet handle, the stylet handle including a handle lumen extending from a distal end of the stylet handle to the opening at the proximal end of the stylet handle, the proximal portion of the stylet wire extending through the handle lumen with the bend located in the opening, wherein the exposed length of the stylet wire is measured from the distal end of the stylet wire to the distal end of the stylet handle.

9. A stylet-lead assembly comprising:
a therapy delivery element comprising a proximal end with a plurality of electrical contacts adapted to electrically couple with an implantable pulse generator, a distal end with a plurality of electrodes electrically coupled to the electrical contacts, and a lumen having a lumen length extending from the proximal end to almost the distal end;

a stylet wire having a distal end and a proximal portion including a proximal, terminal end;

a locking insert having a first channel adapted to receive the proximal portion of the stylet wire, wherein an excess portion of the proximal portion of the stylet wire extending beyond a proximal end of the locking insert includes at least one bend; and a stylet handle having a handle lumen extending from a distal end to an opening at a proximal end, the proximal portion of the stylet wire extending through the handle lumen with the bend located in the opening, the opening adapted to compressively engage the stylet wire to the locking insert to lock the stylet wire with respect to the stylet handle, such that an exposed length of an exposed portion of the stylet wire measured from the distal end of the stylet wire to the distal end of the stylet handle is generally equal to the lumen length, wherein:
the proximal, terminal end of the stylet wire is disposed within the stylet handle; and
with the proximal portion of the stylet wire compressively engaged with the locking insert, the exposed length of the stylet wire is fixed.

10. The stylet-lead assembly of claim 9, comprising a second channel in the locking insert adapted to receive the excess portion of the stylet wire extending beyond the proximal end of the locking insert.

11. The stylet-lead assembly of claim 10, wherein the first channel is generally parallel to the second channel.

12. The stylet-lead assembly of claim 10, wherein the at least one bend of the proximal portion of the stylet wire includes a bend of about 180 degrees between the first channel and the second channel.

13. The stylet-lead assembly of claim 9, wherein the first channel is disposed between a pair of arms adapted to flex inwardly to compressively engage the proximal portion of the stylet wire.

14. A neurostimulation system comprising:
an implantable pulse generator;
a therapy delivery element comprising a proximal end with a plurality of electrical contacts adapted to electrically couple with the implantable pulse generator, a distal end with a plurality of electrodes electrically coupled to the electrical contacts, and a lumen having a lumen length extending from the proximal end to almost the distal end;

a stylet wire having a distal end and a proximal portion including a proximal, terminal end;

a locking insert having a first channel adapted to receive the proximal portion of the stylet wire, wherein an excess portion of the proximal portion of the stylet wire extending beyond a proximal end of the locking insert includes at least one bend; and a stylet handle having an opening at a first end adapted to compressively engage the proximal portion of the stylet wire to the locking insert to lock the stylet wire with respect to the stylet handle, such that an exposed length of an exposed portion of the stylet wire extending distally from the stylet handle is generally equal to the lumen length, wherein:
the proximal, terminal end of the stylet wire is disposed within the stylet handle; and
with the proximal portion of the stylet wire compressively engaged with the locking insert, the exposed length of the stylet wire is fixed.

15. The neurostimulation system of claim 14, wherein the opening is at a proximal end of the stylet handle, the stylet handle including a handle lumen extending from a distal end of the stylet handle to the opening at the proximal end of the stylet handle, the proximal portion of the stylet wire extending through the handle lumen with the bend located in the opening, wherein the exposed length of the stylet wire is measured from the distal end of the stylet wire to the distal end of the stylet handle.

16. The neurostimulation system of claim 14, wherein the locking insert includes a second channel configured to receive the excess portion of the stylet wire extending beyond the proximal end of the locking insert.

17. A neurostimulation system comprising:
- an implantable pulse generator;
- a therapy delivery element comprising a proximal end with a plurality of electrical contacts adapted to electrically couple with the implantable pulse generator, a distal end with a plurality of electrodes electrically coupled to the electrical contacts, and a lumen having a lumen length extending from the proximal end to almost the distal end;
- a stylet wire having a distal end and a proximal portion including a proximal, terminal end;
- a locking insert having a first channel adapted to receive the proximal portion of the stylet wire, wherein an excess portion of the proximal portion of the stylet wire extending beyond a proximal end of the locking insert includes at least one bend; and
- a stylet handle having a handle lumen extending from a distal end to an opening at a proximal end, the proximal portion of the stylet wire extending through the handle lumen with the bend located in the opening, the opening adapted to compressively engage the stylet wire to the locking insert to lock the stylet wire with respect to the stylet handle, such that an exposed length of an exposed portion of the stylet wire measured from the distal end of the stylet wire to the distal end of the stylet handle is generally equal to the lumen length, wherein:
  - the proximal, terminal end of the stylet wire is disposed within the stylet handle; and
  - with the proximal portion of the stylet wire compressively engaged with the locking insert, the exposed length of the stylet wire is fixed.

18. The neurostimulation system of claim 17, wherein the first channel is disposed between a pair of arms adapted to flex inwardly to compressively engage the proximal portion of the stylet wire.

* * * * *

UNITED STATES PATENT AND TRADEMARK OFFICE
CERTIFICATE OF CORRECTION

PATENT NO.         : 8,721,659 B2
APPLICATION NO.    : 13/222018
DATED              : May 13, 2014
INVENTOR(S)        : Elliot Bridgeman et al.

It is certified that error appears in the above-identified patent and that said Letters Patent is hereby corrected as shown below:

In the Claims

Column 9, line 5 (Claim 1, line 10) delete "proximal, terminal" and insert --proximal--

Column 9, line 60 (Claim 9, line 10) delete "proximal, terminal" and insert --proximal--

Column 10, line 9 (Claim 9, line 26) delete "proximal, terminal" and insert --proximal--

Column 10, line 39 (Claim 14, line 11) delete "proximal, terminal" and insert --proximal--

Column 10, line 52 (Claim 14, line 24) delete "proximal, terminal" and insert --proximal--

Column 11, line 12 (Claim 17, line 11) delete "proximal, terminal" and insert --proximal--

Column 12, line 9 (Claim 17, line 27) delete "proximal, terminal" and insert --proximal--

Signed and Sealed this
Twenty-third Day of September, 2014

Michelle K. Lee
*Deputy Director of the United States Patent and Trademark Office*